(12) United States Patent
Firestone

(10) Patent No.: US 11,446,067 B2
(45) Date of Patent: Sep. 20, 2022

(54) DISTAL RADIUS PLATING SYSTEM

(71) Applicant: The Board of Regents of the University of Nebraska, Lincoln, NE (US)

(72) Inventor: Daniel Firestone, Omaha, NE (US)

(73) Assignee: The Board of Regents of The University of Nebraska, Lincoln, NE (US)

( * ) Notice: Subject to any disclaimer, the term of this patent is extended or adjusted under 35 U.S.C. 154(b) by 92 days.

(21) Appl. No.: 16/977,299

(22) PCT Filed: Mar. 1, 2019

(86) PCT No.: PCT/US2019/020342
§ 371 (c)(1),
(2) Date: Sep. 1, 2020

(87) PCT Pub. No.: WO2019/169292
PCT Pub. Date: Sep. 6, 2019

(65) Prior Publication Data
US 2021/0000516 A1 Jan. 7, 2021

Related U.S. Application Data

(60) Provisional application No. 62/637,432, filed on Mar. 2, 2018.

(51) Int. Cl.
*A61B 17/80* (2006.01)
*A61B 17/56* (2006.01)

(52) U.S. Cl.
CPC ...... *A61B 17/8061* (2013.01); *A61B 17/8085* (2013.01); *A61B 2017/564* (2013.01)

(58) Field of Classification Search
CPC . A61B 17/80; A61B 17/8061; A61B 17/8085; A61B 17/809; A61B 2017/564
See application file for complete search history.

(56) References Cited

U.S. PATENT DOCUMENTS 7,153,309 B2 * 12/2006 Huebner ............ A61B 17/1728
606/96
8,529,608 B2 * 9/2013 Terrill .................... A61B 17/88
606/280

(Continued)

FOREIGN PATENT DOCUMENTS

CN 204049818 U 12/2014

OTHER PUBLICATIONS

Notification of Transmittal of the International Search Report and the Written Opinion of the International Searching Authority, or the Declaration dated Jun. 18, 2019 for App. No. PCT/US2019/020342.

*Primary Examiner* — Anu Ramana
(74) *Attorney, Agent, or Firm* — Ryan T. Grace; Advent, LLP

(57) ABSTRACT

Systems and methods are described for treating distal radius fractures using a plating system. In an aspect, a distal radius plating system includes a volar plate body for interfacing with a volar side of a distal portion of a radius bone. The volar plate body has a volar head portion extending from the volar plate body and terminating at a distal edge, the volar head portion including a first set of apertures to receive fixation fasteners therethrough to fix to the radius bone. The distal radius plating system also includes a radial longitudinal portion extending from a radial edge of the volar plate body to interface with the radial styloid of the radius bone while the volar plate body is positioned on the volar side of the distal portion of the radius bone.

18 Claims, 9 Drawing Sheets

(56) References Cited

U.S. PATENT DOCUMENTS

| | | |
|---|---|---|
| 9,333,014 B2 | 5/2016 | Gonzalez-Hernandez |
| 9,603,625 B2* | 3/2017 | Orbay ................ A61B 17/1739 |
| 2008/0119895 A1* | 5/2008 | Manceau ........... A61B 17/8047 |
| | | 606/301 |
| 2012/0016427 A1* | 1/2012 | Stindel ............... A61B 17/8023 |
| | | 606/86 R |
| 2012/0165878 A1 | 6/2012 | Hwa et al. |
| 2013/0041375 A1* | 2/2013 | Fierlbeck ............. A61B 17/809 |
| | | 606/281 |
| 2013/0304138 A1* | 11/2013 | Orbay ...................... A61F 2/30 |
| | | 606/86 R |
| 2014/0214089 A1 | 7/2014 | Glickel |
| 2016/0317205 A1 | 11/2016 | Baker |
| 2018/0092676 A1* | 4/2018 | Ananthan .......... A61B 17/8085 |

* cited by examiner

DISTAL RADIUS PLATING SYSTEM

BACKGROUND

Bone fractures of the wrist typically require stabilization of bone fragments of the distal radius to facilitate proper alignment of bone fragments during the healing process. Stabilization methods can include external fixation techniques (e.g., casting, external fixators) and invasive fixation techniques (pinning/wiring, plating).

SUMMARY

In an aspect, a distal radius plating system includes, but is not limited to, a volar plate body and a radial longitudinal portion extending from the radial edge of the volar plate body. The volar plate body has an exterior surface and a bone-facing surface opposing the exterior surface, a radial edge and an ulnar edge opposing the radial edge, and a proximal edge and a distal edge opposing the proximal edge. The volar plate body is longitudinally disposed between the proximal edge and the distal edge and has a size and shape for interfacing with a volar side of a distal portion of a radius bone via the bone-facing surface. The volar plate body defines a plurality of apertures from the exterior surface to the bone-facing surface to receive fixation fasteners therethrough to fix to the radius bone. The volar plate body has a volar head portion extending from the volar plate body and terminating at the distal edge, where the volar head portion includes a first set of apertures from the exterior surface to the bone-facing surface to receive fixation fasteners therethrough to fix to the radius bone and has a second set of apertures from the exterior surface to the bone-facing surface to receive stabilization wire therethrough to interface with the radius bone. The radial longitudinal portion has a lateral extension portion coupled with the volar plate body and a radial extension portion coupled with the lateral extension portion, where the lateral extension portion curves from the exterior surface toward the bone-facing surface. The radial extension portion extends in a direction from the proximal edge toward the distal edge. The radial extension portion has a radial exterior surface and a radial bone-facing surface opposing the radial exterior surface. The radial extension portion has at least a first aperture from the radial exterior surface to the radial bone-facing surface to receive fixation fasteners therethrough to fix to the radius bone and has at least a second aperture to receive stabilization wire therethrough to interface with the radius bone, wherein at least a portion of the radial bone-facing surface is substantially orthogonal to at least a portion of the bone-facing surface of the volar plate body.

In an aspect, a method of treating a patient having a distal radius fracture using a distal radius plating system includes, but is not limited to, introducing a distal radius plating system to a distal portion of a radius bone of a patient through a volar incision on the patient and securing at least a portion of the distal radius plating system to the distal portion of the radius bone. The distal radius plating system of the method includes, but is not limited to, a volar plate body and a radial longitudinal portion extending from the radial edge of the volar plate body. The volar plate body has an exterior surface and a bone-facing surface opposing the exterior surface, a radial edge and an ulnar edge opposing the radial edge, and a proximal edge and a distal edge opposing the proximal edge. The volar plate body is longitudinally disposed between the proximal edge and the distal edge and has a size and shape for interfacing with a volar side of the distal portion of the radius bone via the bone-facing surface. The volar plate body defines a plurality of apertures from the exterior surface to the bone-facing surface to receive fixation fasteners therethrough to fix to the radius bone. The volar plate body has a volar head portion extending from the volar plate body and terminating at the distal edge, where the volar head portion includes a first set of apertures from the exterior surface to the bone-facing surface to receive fixation fasteners therethrough to fix to the radius bone and has a second set of apertures from the exterior surface to the bone-facing surface to receive stabilization wire therethrough to interface with the radius bone. The radial longitudinal portion has a lateral extension portion coupled with the volar plate body and a radial extension portion coupled with the lateral extension portion, where the lateral extension portion curves from the exterior surface toward the bone-facing surface. The radial extension portion extends in a direction from the proximal edge toward the distal edge. The radial extension portion has a radial exterior surface and a radial bone-facing surface opposing the radial exterior surface. The radial extension portion has at least a first aperture from the radial exterior surface to the radial bone-facing surface to receive fixation fasteners therethrough to fix to the radius bone and has at least a second aperture to receive stabilization wire therethrough to interface with the radius bone, wherein at least a portion of the radial bone-facing surface is substantially orthogonal to at least a portion of the bone-facing surface of the volar plate body.

DRAWINGS

The Detailed Description is described with reference to the accompanying figures. The use of the same reference numbers in different instances in the description and the figures may indicate similar or identical items.

DETAILED DESCRIPTION

Figure 1:
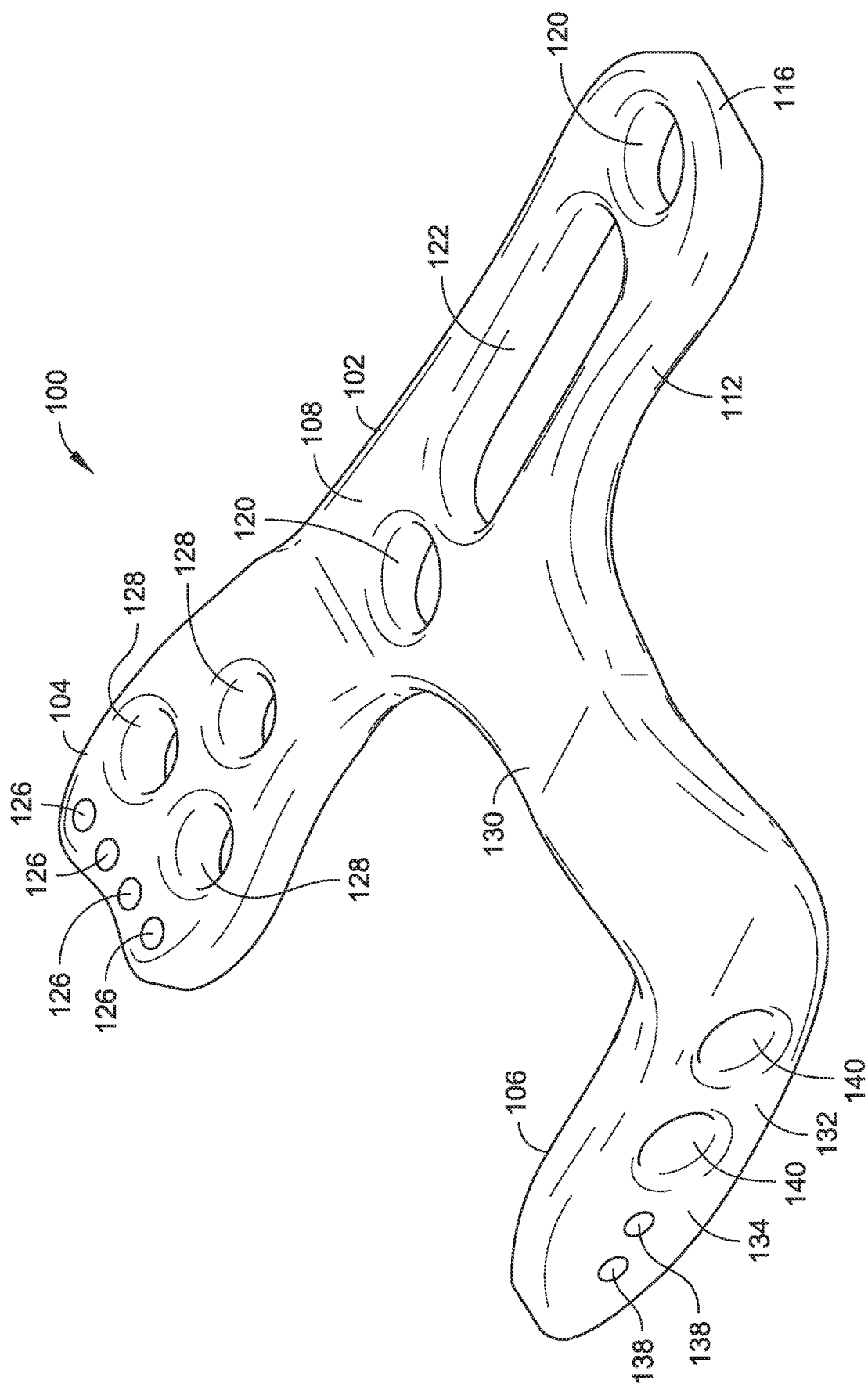
FIG. 1 is an isometric view of a distal radius plating system in accordance with an example embodiment of the present disclosure, shown in a left-handed configuration.

Distal radius fractures, or fractures of the wrist, can result from external forces applied to the wrist, such as through physical trauma caused by a fall or other impact to the arm, wrist, or hand. Such forces can cause portions of the wrist to break into fragments, particularly for bones susceptible to fracture (e.g., those affected by osteoporosis or the like). For instance, distal radial fractures can include intra-articular fractures resulting in fragments of the radial styloid, lunate fossa, etc. Such fragmentation can include comminuted fracture patterns, requiring dedicated alignment, fixation, or stabilization systems to treat the injury by moving the fragments back into proper position (a "reduction" technique) and preventing the fragments from moving out of position during the healing process. If untreated or improperly aligned, the bone fragments may not be in proper position during the healing process, which can result in pain or discomfort, reduction in range of motion, and other symptoms. Alignment, fixation, or stabilization techniques include casting, external fixation, internal pinning/wiring, and internal plating. Casting techniques provide an external fixation technique via substantially rigid external casts in an attempt to stabilize internal wrist fractures, but often lack the precision to treat complex fractures such as comminuted fractures or other fragmentation. External fixators provide tension to ligaments surrounding the wrist fracture in an attempt to bring the fragments into alignment, but as with casting, often lack the requisite precision to properly align multiple distal radius fragments. Pinning and wiring techniques provide invasive alignment and fixation methods by utilizing pins and/or wires to hold fragments relative to other fragments or other portions of the wrist. These techniques can introduce inconsistencies in surgical applications between differing surgeons or between differing patients, which can provide inconsistent treatment results. Further, the pinning and wiring may be insufficient to stably fix bone fragments when the area surrounding the fragments includes additional fragments (e.g., comminuted bone) or is osteoporotic (e.g., lacking proper structural bone support). Internal plating involves introducing and fixing a plate to a bone surface, such as the dorsal or volar side of the radius, and introducing screws through the plating into the bone fragments to fix them relative to the bone. Other plating utilizes fragment specific plating over other portions of the distal radius, however such fragment specific plating can increase the amount of hardware needed to secure the plating relative to a volar plating system, or can increase the risk for flexor tendon irritation and/or rupture.

Referring generally to FIGS. 1 through 9, systems and methods for treating distal radius fractures using a distal radius plating system are described. The distal radius plating systems and methods provide a comprehensive treatment to distal radius fractures through application of a volar plate body with a volar head portion and a radial longitudinal portion. The volar head portion supports and stabilizes volar distal radial fractures while the radial longitudinal portion supports the radial distal portion of the radius to stabilize and fix fragments radially while the volar plate body and the volar head portion simultaneously provide the volar support. For example, the radial longitudinal portion controls positioning of a radial styloid fragment and the volar head portion or a buttress thereof can control volar ulnar corner and lunate facet fixation. Further, the distal radius plating system can facilitate dorsal ulnar corner fragment stabilization through application of anatomically placed volar to dorsal screws (e.g., via the volar head portion) and suture rope with attached brad or button. Still further, the distal radius plating system can facilitate radial column/radial fragment stabilization through a combination of radial to ulnar screws (e.g., via the radial longitudinal portion) and securing wire (e.g., Kirschner or K-wire).

The radial longitudinal portion extends from the volar plate body longitudinally along the radial side, which keeps plating away from the region of the wrist occupied by the flexor tendons and the flexor pollicis longus, thereby reducing the likelihood of flexor tendon irritation, flexor tendon rupture, or flexor pollicis longus rupture resulting from inefficient distal radial plating systems. The connection of the radial longitudinal portion to the volar plate body provides structure stability to the radial longitudinal portion, thus limiting the amount or number of screws utilized for radial styloid fragment fixation or radial fracture fixation, while avoiding hardware utilized for oblique-angled screws directed at the radial styloid from a volar-based plate. The distal radius plating systems described herein can be introduced to the distal radius of a patient through a volar incision on the patient, thereby enabling radial longitudinal fixation of a radial styloid fragment or a radial styloid fracture through an incision type that is a standard for many surgeons for volar fixation.

Figure 5:
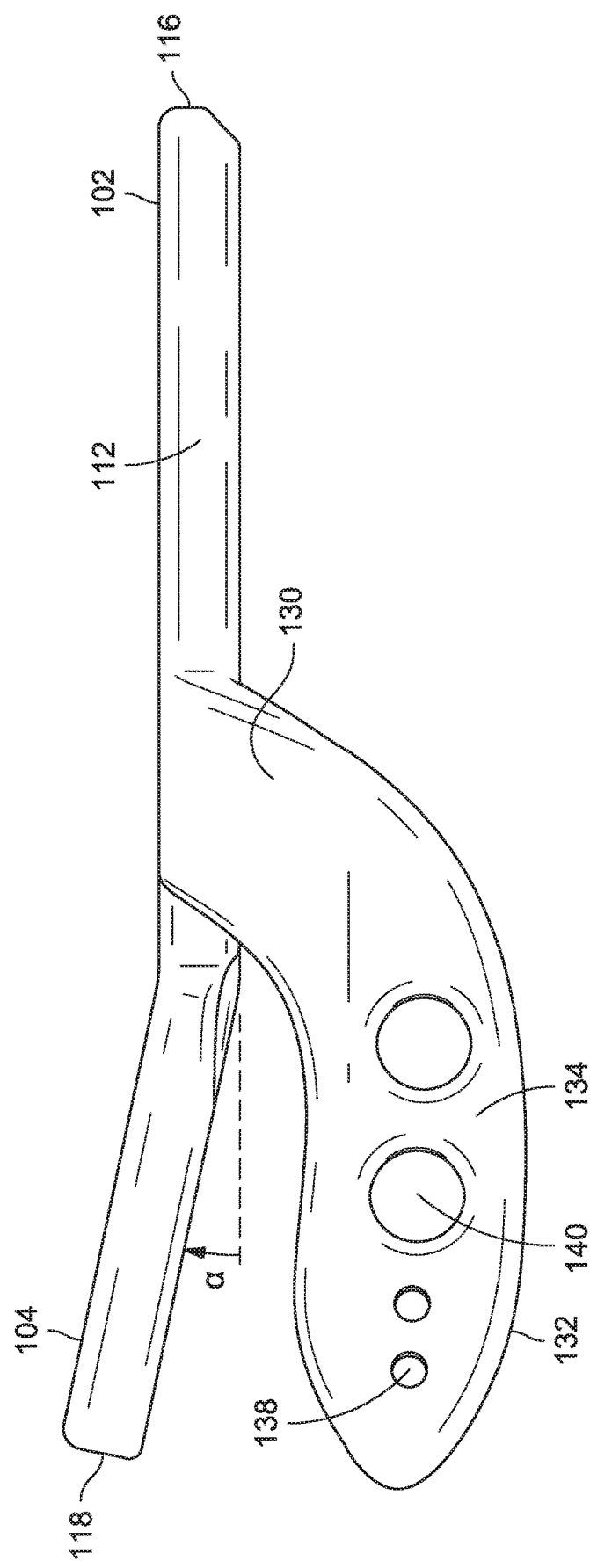
FIG. 5 is a side view of the distal radius plating system of FIG. 1 shown in a left-handed configuration, viewed from the radial side.
Figure 6:
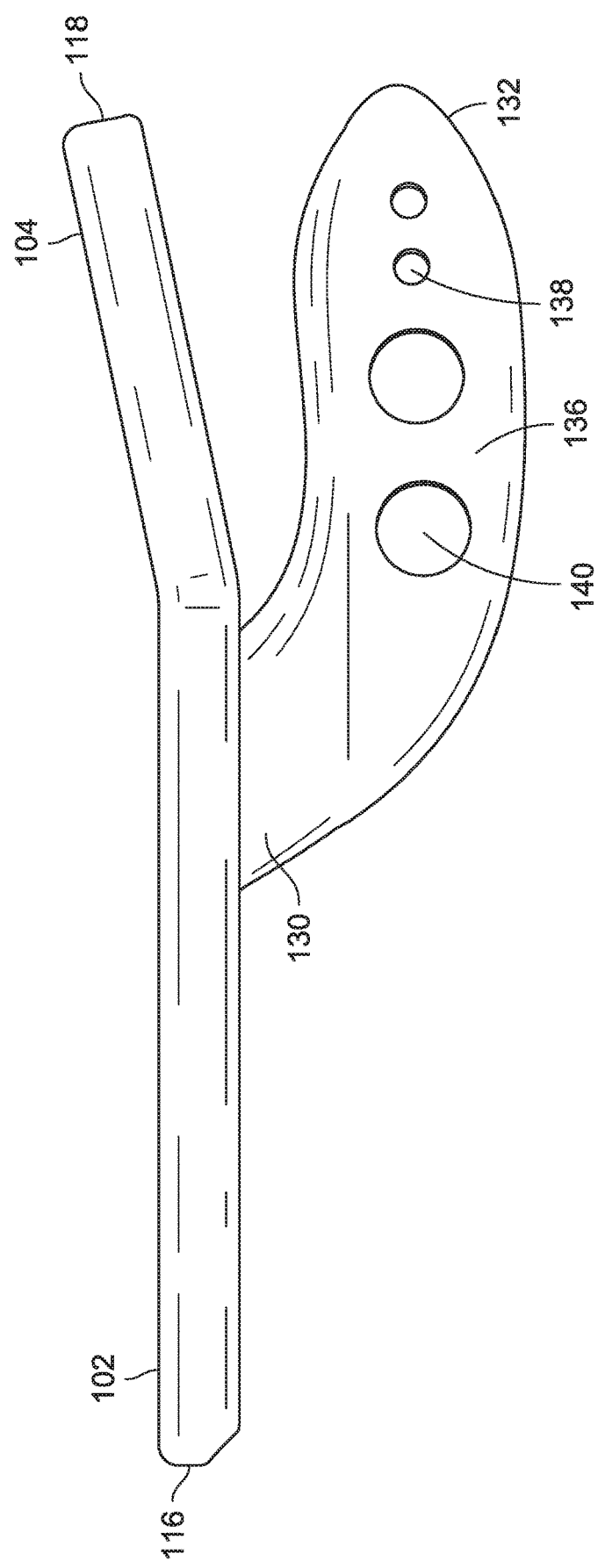
FIG. 6 is a side view of the distal radius plating system of FIG. 1 shown in a left-handed configuration, viewed from the ulnar side.
Figure 7:
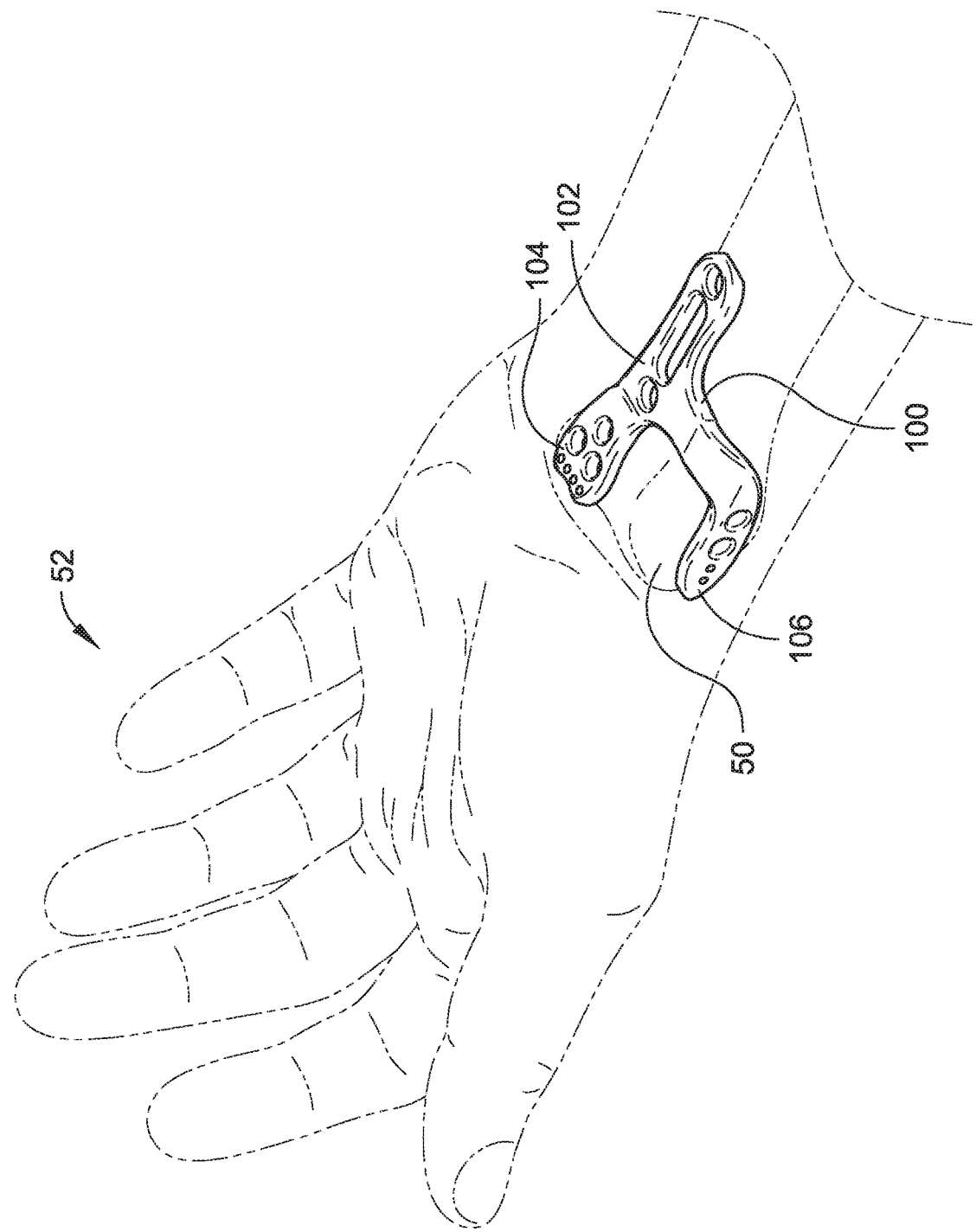
FIG. 7 is environmental view of the distal radius plating system of FIG. 1 in position on a radius bone of a patient.
Figure 8:
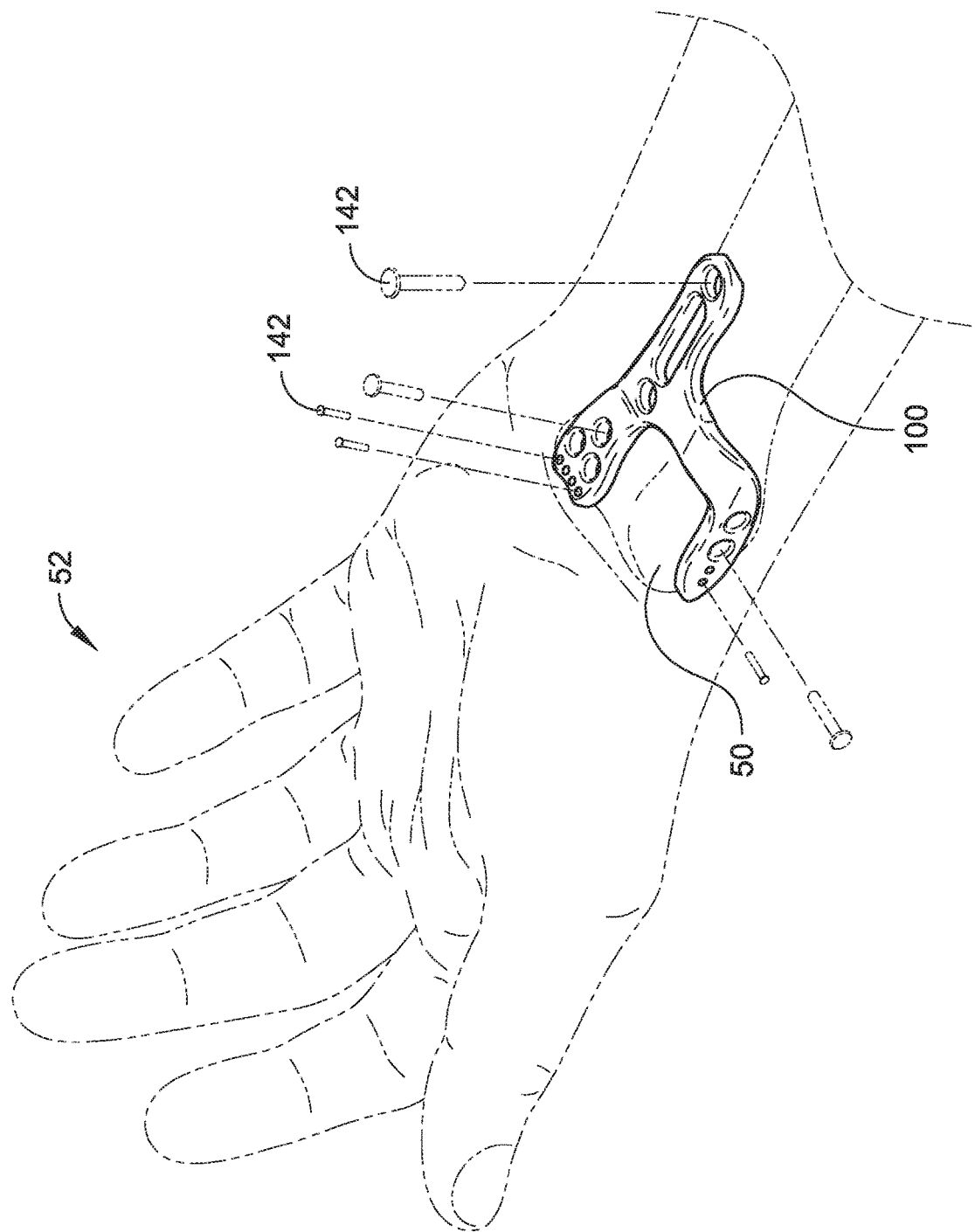
FIG. 8 is an exploded environmental view of the distal radius plating system of FIG. 7, showing fixation fasteners utilized to secure the distal radius plating system to the radius bone or fragments thereof.
Figure 9:
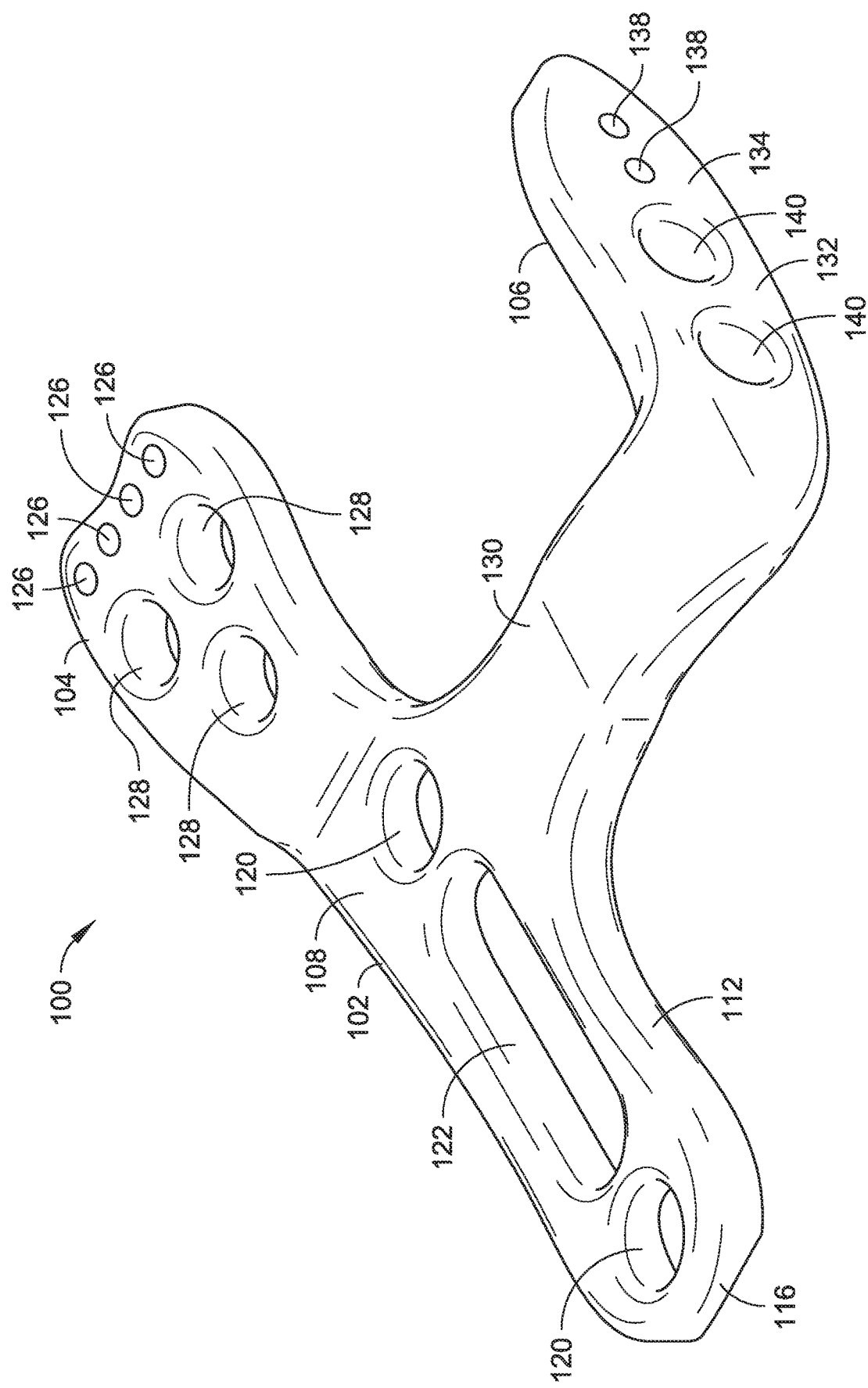
FIG. 9 is an isometric view of a distal radius plating system in accordance with an example embodiment of the present disclosure, shown in a right-handed configuration.

Referring to FIGS. 1 through 9, distal radius plating systems 100 are described. A distal radius plating system ("system 100") includes a volar plate body 102 for positioning against a radius bone of a patient, specifically applied to the volar distal radius. The system 100 shown in FIGS. 1 through 8 is provided as a left-handed configuration. The system 100 shown in FIG. 9 is provided as a right-handed configuration. The system 100 includes a volar head portion 104 and a radial longitudinal portion 106 extending from the volar plate body 102. The volar plate body 102 provides a platform to assist with stabilization of the volar head portion 104 and of the radial longitudinal portion 106 as the volar head portion 104 is applied to the distal radius to stabilize and fix fractures and fragments from the volar side of the radius and as the radial longitudinal portion 106 is applied to the radial distal portion of the radius to stabilize and fix fractures and fragments radially. FIGS. 7 and 8 show an example installation of the system 100 on a radius bone 50 of a patient 52, e.g., as applied through a volar incision on the patient 52.

Figure 2:
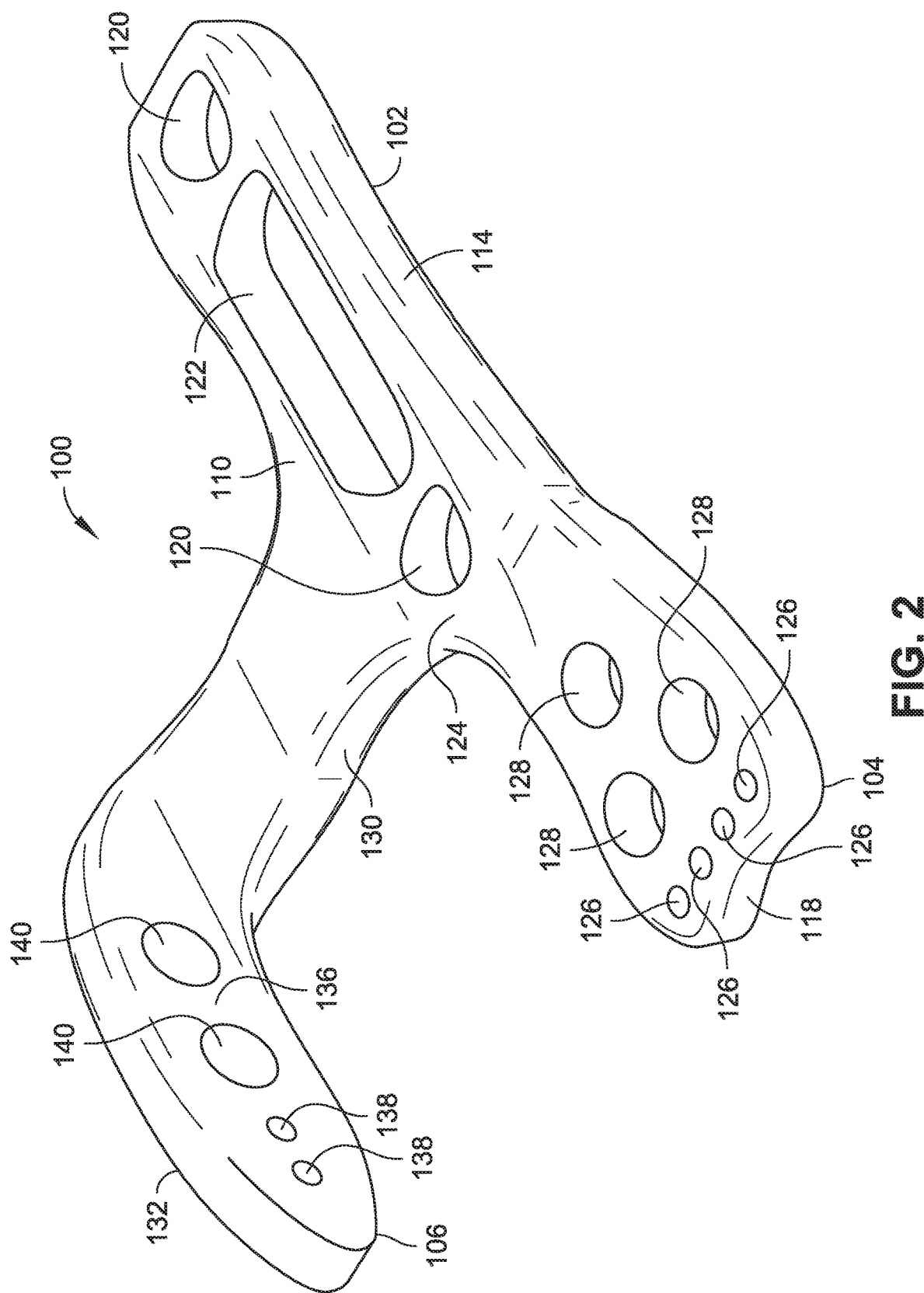
FIG. 2 is an isometric view of the distal radius plating system of FIG. 1 illustrating the bone-facing surfaces.

The volar plate body 102 generally includes an exterior surface 108 and an opposing bone-facing surface 110 (e.g., shown in FIG. 2), a radial edge 112 and an opposing ulnar edge 114 (e.g., shown in FIG. 2), and a proximal edge 116 and opposing distal edge 118 (e.g., shown in FIG. 2). The volar plate body 102 is generally longitudinally disposed between the proximal edge 116 and the distal edge 118 and includes a size and shape for interfacing with a volar side of a distal portion of a radius bone via the bone-facing surface 110. The volar plate body 102 defines a plurality of apertures to receive fixation fasteners (e.g., pegs, screws, pins, wires, etc.) to be introduced to the underlying bone and held against the exterior surface 108. For example, apertures 120 and 122 are shown, where apertures 120 receive a fixation fastener in a generally fixed position through a circular-shaped opening and where aperture 122 provides an elongated opening to receive a fixation fastener. The elongated opening of aperture 122 can permit generally longitudinal movement of the volar plate body 102 relative to the fixation fastener within the aperture 122 prior to securing the fastener (e.g., a fastener head thereof) against the exterior surface 108 of the volar plate body 102. While three apertures are shown positioned through the volar plate body 102, the present disclosure is not limited to three apertures, and can include fewer than three apertures through the volar plate body 102 (e.g., one aperture or two apertures) or more than three apertures (e.g., four apertures, five apertures, six apertures, etc.) to provide the desired level of fixation of the volar plate body 102 relative to the radius. Further, while the apertures 120 are shown as generally circular apertures, the apertures 120 are not limited to circular cross sections and can have other cross-sectional shapes depending on the type of fixation fastener utilized, including, but not limited to, slotted, triangular, rectangular, pentagonal, hexagonal, and so forth.

In implementations, the volar plate body 102 defines a longitudinal channel 124 (e.g., shown in FIG. 2) on the bone-facing surface 110 to interface with at least a portion of the radius bone. For example, the longitudinal channel 124 can provide a contoured surface into which a volar portion of the radius bone can be inserted, such as to provide stability, fit, and assisted alignment of the system 100 for a surgeon during installation. The longitudinal channel 124 can traverse the bone-facing surface 110 of the volar plate body 102 from the proximal edge 116 toward the distal edge 118. For example, the longitudinal channel 124 is shown as originating at the proximal edge 116 and terminating at a portion of the volar head portion 104.

Figure 3:
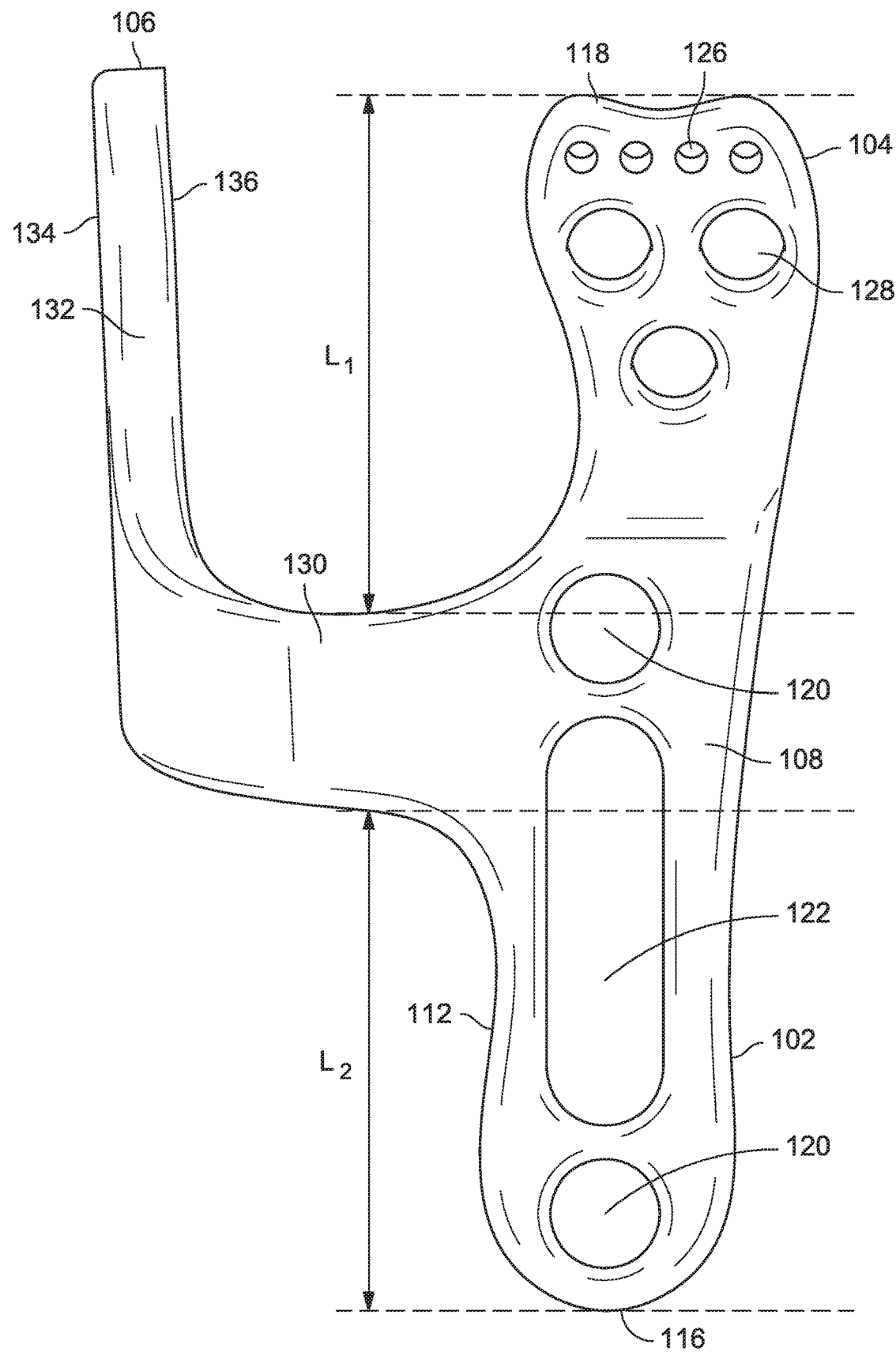
FIG. 3 is a top view of the distal radius plating system of FIG. 1.

The volar head portion 104 extends from the volar plate body 102 and terminates at the distal edge 118. In implementations, the volar head portion 104 is laterally offset toward the ulnar edge 114 (e.g., towards the ulna when in position on the radius) relative to the general longitudinal direction of the volar plate body 102 (e.g., as shown in FIG. 3). The offset of the volar head portion 104 with respect to the volar plate body 102 can provide spacing between the volar head portion 104 and the radial longitudinal portion 106 to accommodate the region of the wrist occupied by the flexor tendons and the flexor pollicis longus. For instance, the relative positioning of the volar head portion 104 and the radial longitudinal portion 106 can provide a lack of plating at the region of the wrist occupied by the flexor tendons and the flexor pollicis longus, thereby reducing the likelihood of flexor tendon irritation, flexor tendon rupture, or flexor pollicis longus rupture, while still providing longitudinal fixation support at the radial side of the distal radius.

The volar head portion 104 defines a plurality of apertures to receive fixation fasteners (e.g., pegs, screws, pins, wires, etc.) to be introduced to the underlying bone and held against the exterior surface 108. For example, two sets of apertures are shown, apertures 126 and apertures 128. Apertures 126 are shown having a generally circular cross-section that has a cross-sectional area that is less than the generally circular cross-section of apertures 128. For instance, the apertures 126 extend from the exterior surface 108 to the bone-facing surface 110 to receive stabilization wire (e.g., K-wire) or other fixation fastener to interface with the distal radius bone and fragments thereof. The smaller aperture size can facilitate precision fasteners to fix and stabilize the relatively small distal radius fragments or comminuted fragments that can occur with wrist fractures. The apertures 128 extend from the exterior surface 108 to the bone-facing surface 110 to receive screws, pegs, or other fixation fastener to interface with the distal radius bone and fragments thereof. The volar head portion 104 is shown with four apertures 126 laterally arranged with respect to each other at the distal end of the volar head portion 104. Alternatively or additionally, the volar head portion 104 can include or support one or more buttresses to extend support surfaces to areas of the distal radius, where such buttresses can include apertures (e.g., apertures 126) to receive fixation fasteners to fix and stabilize fragments adjacent to the buttresses. For example, the volar head portion 104 or one or more buttresses thereof can extend to the volar ulnar corner of the distal radius to support, fix, and stabilize fractures and fragments in that region via introduction of fixation fasteners to the aperture(s) (e.g., aperture 126) to facilitate volar ulnar fixation and lunate facet fixation. In implementations, dorsal ulnar corner fragment stabilization is facilitated through application of anatomically placed volar to dorsal screws through the volar head portion 104 with application of suture rope with attached brad or button. While four apertures 126 are shown positioned through the volar head portion 104, the present disclosure is not limited to four apertures 126, and can include fewer than four apertures 126 through the volar head portion 104 (e.g., one aperture, two apertures, or three apertures) or more than four apertures 126 (e.g., five apertures, six apertures, seven apertures, etc.) to provide the desired level of fixation of the volar head portion 104 relative to the radius and fragments thereof.

The apertures 128 are shown having two apertures 128 laterally disposed with respect to each other and one aperture 128 offset longitudinally toward the proximal edge 116 of the volar plate body 102 in a generally triangular arrangement of apertures 128. While three apertures 128 are shown in the generally triangular arrangement, other patterns of apertures 128 can be utilized to support the volar head portion 104 relative to the distal radius. For instance, additional apertures 128 can be included to provide a surgeon with options for desired regions of fixation to the underlying bone depending upon the location of fractures or fragments of the wrist. Further, while the apertures 126 and 128 are shown as generally circular apertures, the apertures 126 and 128 are not limited to circular cross sections and can have other cross-sectional shapes depending on the type of fixation fastener utilized, including, but not limited to, slotted, triangular, rectangular, pentagonal, hexagonal, and so forth.

In implementations, at least a portion of the volar head portion 104 is vertically displaced from the volar plate body 102 to contour to the surface of the radius as the radius extends from the radial column to the distal end. For example, as shown in FIG. 7, the volar head portion 104 is angled outwardly (shown as angle α) from the volar plate body 102 in a direction from the bone-facing surface 110 to the exterior surface 108. In implementations, the angle α is from approximately 15 degrees to approximately 30 degrees displaced from the volar plate body 102.

The system 100 includes the radial longitudinal portion 106 extending from the radial edge 112 of the volar plate body 102 to provide longitudinal fixation along the radial side of the distal radius while avoiding plating at the region of the wrist occupied by the flexor tendons and the flexor pollicis longus. As shown, the radial longitudinal portion 106 includes a lateral extension portion 130 and a radial extension portion 132. The lateral extension portion 130 is coupled with the volar plate body 102 and the radial extension portion 132 is coupled with the lateral extension portion 130 to form a cohesive plating system for securing to each of the volar distal radius and the radial side distal radius simultaneously. The radial longitudinal portion 106 curves out from the plane of the volar plate body to provide a bone-facing surface against the radial side of the distal radius. For instance, the lateral extension portion 130 curves from the volar plate body 102 in a direction from the exterior surface 108 toward the bone-facing surface 110 to position the radial extension portion 132 along the radial side of the distal radius. As shown in FIG. 3, the lateral extension portion 130 laterally extends from the radial edge 112 of the volar plate body 102 at an intermediate portion of the radial edge 112 between the proximal edge 116 and the distal edge 118. For example, the intermediate portion is approximately at a middle portion of the radial edge 112 between the proximal edge 116 and the distal edge 118 (shown between $L_1$ and $L_2$ in FIG. 3).

Figure 4:
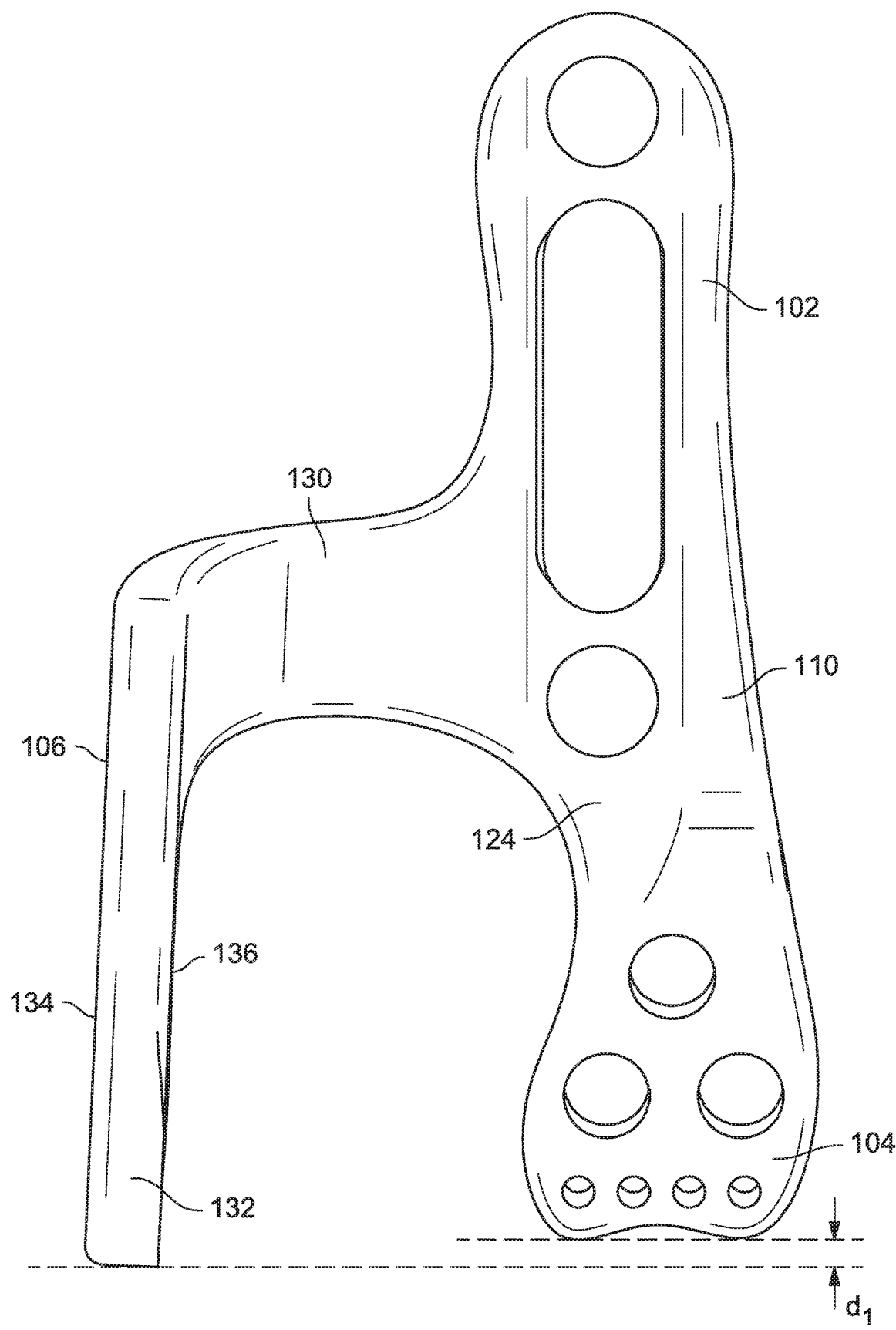
FIG. 4 is a bottom view of the distal radius plating system of FIG. 1.

The radial extension portion 132 extends longitudinally from the lateral extension portion 130 in a direction from the proximal edge 116 toward the distal edge 118. The radial extension portion 132 includes a radial exterior surface 134 and an opposing radial bone-facing surface 136 (e.g., shown in FIG. 2). As shown in FIG. 4, the radial exterior surface 134 and the radial bone-facing surface 136 are substantially orthogonal (e.g., from 80 degrees to 100 degrees offset) to at least a portion of the bone-facing surface 110 of the volar plate body 104 to permit interfacing with each of the volar distal radius and the radial side distal radius simultaneously. For example, the volar plate body 102 can define a longitudinal plane extending between the external surface 108 and the bone-facing surface 110, where the radial bone-facing surface 136 is positioned substantially orthogonally to the longitudinal plane. Since the bone surface of the radial side of the distal radius can have more contours or curves than the radial column to which the volar plate body 102 can be secured, the radial extension portion 132 may be curved (e.g., on the radial bone-facing surface 136) to conform to such contours or curves. For instance, the radial extension portion 132 can include malleable materials (e.g., surgical grade metals) having a thickness suitable for bending into shape prior to or during the surgical installation procedure to conform the radial extension portion 132 to the bone surface of the radial side of the distal radius. The radial longitudinal portion 106 has a size and shape to interface the radial extension portion 132 with a radial styloid portion or a radial styloid fragment of the radius bone while the volar plate body 102 interfaces with the volar side of the distal portion of the radius bone. In implementations, an example of which is shown in FIGS. 4-6, the distal edge of the radial extension portion 132 extends beyond the distal edge of the volar head portion 104 (e.g., shown as di in FIG. 4) when positioned at the distal radius, such as to provide additional support to the radial styloid which projects beyond the other bone surfaces of at the distal radius. In implementations, the volar head portion 104 has a size and shape to bring at least a portion of the distal edge 118 in contact with the radius bone adjacent to the lunate facet while the radial extension portion 132 interfaces with a radial styloid portion or a radial styloid fragment of the radius bone. In implementations, the volar head portion 104 has a size and shape to bring at least a portion of the distal edge 118 in contact with a volar ulnar portion or a volar ulnar fragment of the radius bone while the radial extension portion 132 interfaces with a radial styloid portion or a radial styloid fragment of the radius bone. In implementations, the volar head portion 104 has a size and shape to bring at least a portion of the distal edge 118 adjacent to a watershed line of the radius bone at a volar ulnar corner but not at the watershed line of the radius bone at a radial side of the radius bone while the radial extension portion 132 interfaces with a radial styloid portion or a radial styloid fragment of the radius bone. Such a configuration can prevent plating being present at the region of the wrist occupied by the flexor tendons and the flexor pollicis longus.

The radial extension portion 132 defines a plurality of apertures to receive fixation fasteners (e.g., pegs, screws, pins, wires, etc.) to be introduced to the underlying bone and held against the radial exterior surface 134. For example, two sets of apertures are shown, apertures 138 and apertures 140. Apertures 138 are shown having a generally circular cross-section that has a cross-sectional area that is less than the generally circular cross-section of apertures 140. For instance, the apertures 138 extend from the radial exterior surface 134 to the radial bone-facing surface 136 to receive stabilization wire (e.g., K-wire) or other fixation fastener to interface with the distal radius bone and fragments thereof. The smaller aperture size can facilitate precision fasteners to fix and stabilize from the radial side the relatively small distal radius fragments or comminuted fragments that can occur with wrist fractures. The apertures 140 extend from the radial exterior surface 134 to the radial bone-facing surface 136 to receive screws, pegs, or other fixation fastener to interface with the distal radius bone and fragments thereof from the radial side of the bone. The radial extension portion 132 is shown with four apertures (e.g., two apertures 138 and two apertures 140) longitudinally arranged with respect to each other at the distal end of the radial extension portion 132. While four apertures are shown positioned through the radial extension portion 132, the present disclosure is not limited to four apertures, and can include fewer than four apertures through the radial extension portion 132 (e.g., one aperture, two apertures, or three apertures) or more than four apertures (e.g., five apertures, six apertures, seven apertures, etc.) to provide the desired level of fixation of the radial extension portion 132 relative to the radial side of the distal radius and fragments thereof. Further, while the radial extension portion 132 is shown with a longitudinal arrangement of apertures, other patterns of apertures 138 and 140 can be utilized to support the radial extension portion 132 relative to the radial side of the distal radius. For instance, additional apertures 138 or 140 can be included to provide a surgeon with options for desired regions of fixation to the underlying bone depending upon the location of fractures or fragments of the wrist. Further, while the apertures 138 and 140 are shown as generally circular apertures, the apertures 138 and 140 are not limited to circular cross sections and can have other cross-sectional shapes depending on the type of fixation fastener utilized, including, but not limited to, slotted, triangular, rectangular, pentagonal, hexagonal, and so forth.

The system 100 can be introduced to the radius bone of the patient through a volar incision on the patient, where the volar plate body 102 and volar head portion 104 can be secured to volar side of the underlying radius bone (e.g., via one or more fixation fasteners 142, such as a peg or screw, as shown in FIG. 8) and where the radial extension portion 132 can be secured to the radial side of the underlying radius bone (e.g., via one or more fixation fasteners 142, such as a peg or screw, as shown in FIG. 8) through the same volar incision. As such, the system 100 can facilitate radial longitudinal fixation of a radial styloid fragment or a radial styloid fracture through an incision type (i.e., volar incision) that is a standard for many surgeons for volar fixation.

The system 100 is generally constructed from surgical grade materials (e.g., biocompatible materials) where such materials have a strength and rigidity to support the volar plate body 102, the volar head portion 104, and the radial longitudinal portion 106 relative to the underlying portions of the distal radius, including fractures or fragments thereof. As an example, the system 100 can be constructed from surgical grade titanium or alloys thereof, stainless steel, cobalt chromium alloys, or combinations thereof. The system 100 can be formed from a single piece construction and bent or otherwise shaped into the conformations described herein. Alternatively, portions of the system 100 can be separately formed and fused or otherwise bonded to other portions of the system 100.

Although the subject matter has been described in language specific to structural features and/or process operations, it is to be understood that the subject matter defined in the appended claims is not necessarily limited to the specific features or acts described above. Rather, the specific features and acts described above are disclosed as example forms of implementing the claims.

What is claimed is:

1. A distal radius plating system, comprising:
a volar plate body,
   the volar plate body having
      an exterior surface and a bone-facing surface opposing the exterior surface,
      a radial edge and an ulnar edge opposing the radial edge, and
      a proximal edge and a distal edge opposing the proximal edge,
   the volar plate body longitudinally disposed between the proximal edge and the distal edge and having a size and shape for interfacing with a volar side of a distal portion of a radius bone via the bone-facing surface, the volar plate body defining a plurality of apertures from the exterior surface to the bone-facing surface to receive fixation fasteners therethrough to fix to the radius bone,
   the volar plate body having a volar head portion extending from the volar plate body and terminating at the distal edge, the volar head portion including a first set of apertures from the exterior surface to the bone-facing surface to receive fixation fasteners therethrough to fix to the radius bone and having a second set of apertures from the exterior surface to the bone-facing surface to receive stabilization wire therethrough to interface with the radius bone; and
   a radial longitudinal portion extending from the radial edge of the volar plate body, the radial longitudinal portion having a lateral extension portion coupled with the volar plate body and a radial extension portion coupled with the lateral extension portion, the lateral extension portion curving from the exterior surface toward the bone-facing surface, the radial extension portion extending in a direction from the proximal edge toward the distal edge, the radial extension portion having a radial exterior surface and a radial bone-facing surface opposing the radial exterior surface, the radial extension portion having at least a first aperture from the radial exterior surface to the radial bone-facing surface to receive fixation fasteners therethrough to fix to the radius bone and having at least a second aperture to receive stabilization wire therethrough to interface with the radius bone, the radial longitudinal portion having a size and shape to interface the radial extension portion with a radial styloid portion or a radial styloid fragment of the radius bone while the volar plate body interfaces with the volar side of the distal portion of the radius bone, wherein at least a portion of the radial bone-facing surface is substantially orthogonal to at least a portion of the bone-facing surface of the volar plate body.

2. The distal radius plating system of claim 1, wherein the lateral extension portion laterally extends from the radial edge of the volar plate body at an intermediate portion of the radial edge between the proximal edge and the distal edge.

3. The distal radius plating system of claim 2, wherein the intermediate portion is approximately at a middle portion of the radial edge between the proximal edge and the distal edge.

4. The distal radius plating system of claim 1, wherein the volar head portion has a size and shape to bring at least a portion of the distal edge in contact with the radius bone adjacent to the lunate facet.

5. The distal radius plating system of claim 1, wherein the volar head portion has a size and shape to bring at least a portion of the distal edge in contact with a volar ulnar portion or a volar ulnar fragment of the radius bone.

6. The distal radius plating system of claim 1, wherein the volar head portion has a size and shape to extend least a portion of the distal edge adjacent to a watershed line of the radius bone at a volar ulnar corner but not at the watershed line of the radius bone at a radial side of the radius bone.

7. The distal radius plating system of claim 1, wherein the volar plate body defines a longitudinal channel on the bone-facing surface, the longitudinal channel having a size and shape to interface with at least a portion of the radius bone.

8. The distal radius plating system of claim 1, wherein at least a portion of the volar head portion is angled outwardly from the volar plate body from the bone-facing surface to the exterior surface.

9. A distal radius plating system, comprising:
a volar plate body,
   the volar plate body having
      an exterior surface and a bone-facing surface opposing the exterior surface,
      a radial edge and an ulnar edge opposing the radial edge, and
      a proximal edge and a distal edge opposing the proximal edge,
   the volar plate body longitudinally disposed between the proximal edge and the distal edge and having a size and shape for interfacing with a volar side of a distal portion of a radius bone via the bone-facing surface, the volar plate body defining a plurality of apertures from the exterior surface to the bone-facing surface to receive fixation fasteners therethrough to fix to the radius bone,
   the volar plate body having a volar head portion extending from the volar plate body and terminating at the distal edge, the volar head portion including a first set of apertures from the exterior surface to the bone-facing surface to receive fixation fasteners therethrough to fix to the radius bone and having a second set of apertures from the exterior surface to the bone-facing surface to receive stabilization wire therethrough to interface with the radius bone; and
   a radial longitudinal portion extending from the radial edge of the volar plate body, the radial longitudinal portion having a lateral extension portion coupled with the volar plate body and a radial extension portion coupled with the lateral extension portion, the lateral extension portion curving from the exterior surface toward the bone-facing surface, the radial extension portion extending in a direction from the proximal edge toward the distal edge, the radial extension portion having a radial exterior surface and a radial bone-facing surface opposing the radial exterior surface, the radial extension portion having at least a first aperture from the radial exterior surface to the radial bone-facing surface to receive fixation fasteners therethrough to fix to the radius bone and having at least a second aperture to receive stabilization wire therethrough to interface with the radius bone, wherein the first aperture of the radial extension portion has a larger cross-sectional area than the second aperture of the radial extension portion, and wherein at least a portion of the radial bone-facing surface is substantially orthogonal to at least a portion of the bone-facing surface of the volar plate body.

10. A method of treating a patient having a distal radius fracture using a distal radius plating system, comprising:
introducing a distal radius plating system to a distal portion of a radius bone of a patient through a volar incision on the patient, the distal radius plating system including
a volar plate body,
the volar plate body having
an exterior surface and a bone-facing surface opposing the exterior surface,
a radial edge and an ulnar edge opposing the radial edge,
a proximal edge and a distal edge opposing the proximal edge,
the volar plate body longitudinally disposed between the proximal edge and the distal edge and having a size and shape for interfacing with a volar side of the distal portion of the radius bone via the bone-facing surface, the volar plate body defining a plurality of apertures from the exterior surface to the bone-facing surface to receive fixation fasteners therethrough to fix to the radius bone,
the volar plate body having a volar head portion extending from the volar plate body and terminating at the distal edge, the volar head portion including a first set of apertures from the exterior surface to the bone-facing surface to receive fixation fasteners therethrough to fix to the radius bone and having a second set of apertures from the exterior surface to the bone-facing surface to receive stabilization wire therethrough to interface with the radius bone, and
a radial longitudinal portion extending from the radial edge of the volar plate body, the radial longitudinal portion having a lateral extension portion coupled with the volar plate body and a radial extension portion coupled with the lateral extension portion, the lateral extension portion curving from the exterior surface toward the bone-facing surface, the radial extension portion extending in a direction from the proximal edge toward the distal edge, the radial extension portion having a radial exterior surface and a radial bone-facing surface opposing the radial exterior surface, the radial extension portion having at least a first aperture from the radial exterior surface to the radial bone-facing surface to receive fixation fasteners therethrough to fix to the radius bone and having at least a second aperture to receive stabilization wire therethrough to interface with the radius bone, wherein the first aperture of the radial extension portion has a larger cross-sectional area than the second aperture of the radial extension portion, wherein at least a portion of the radial bone-facing surface is substantially orthogonal to at least a portion of the bone-facing surface of the volar plate body; and
securing at least a portion of the distal radius plating system to the distal portion of the radius bone.

11. A method of treating a patient having a distal radius fracture using a distal radius plating system, comprising:
introducing a distal radius plating system to a distal portion of a radius bone of a patient through a volar incision on the patient, the distal radius plating system including
a volar plate body,
the volar plate body having
an exterior surface and a bone-facing surface opposing the exterior surface,
a radial edge and an ulnar edge opposing the radial edge,
a proximal edge and a distal edge opposing the proximal edge,
the volar plate body longitudinally disposed between the proximal edge and the distal edge and having a size and shape for interfacing with a volar side of the distal portion of the radius bone via the bone-facing surface, the volar plate body defining a plurality of apertures from the exterior surface to the bone-facing surface to receive fixation fasteners therethrough to fix to the radius bone,
the volar plate body having a volar head portion extending from the volar plate body and terminating at the distal edge, the volar head portion including a first set of apertures from the exterior surface to the bone-facing surface to receive fixation fasteners therethrough to fix to the radius bone and having a second set of apertures from the exterior surface to the bone-facing surface to receive stabilization wire therethrough to interface with the radius bone, and
a radial longitudinal portion extending from the radial edge of the volar plate body, the radial longitudinal portion having a lateral extension portion coupled with the volar plate body and a radial extension portion coupled with the lateral extension portion, the lateral extension portion curving from the exterior surface toward the bone-facing surface, the radial extension portion extending in a direction from the proximal edge toward the distal edge, the radial extension portion having a radial exterior surface and a radial bone-facing surface opposing the radial exterior surface, the radial extension portion having at least a first aperture from the radial exterior surface to the radial bone-facing surface to receive fixation fasteners therethrough to fix to the radius bone and having at least a second aperture to receive stabilization wire therethrough to interface with the radius bone, wherein at least a portion of the radial bone-facing surface is substantially orthogonal to at least a portion of the bone-facing surface of the volar plate body;
introducing the radial extension portion of the distal radius plating system to a radial styloid portion or a radial styloid fragment of the radius bone while simultaneously introducing the bone-facing surface of the volar plate body to the volar side of the distal portion of the radius bone; and
securing at least a portion of the distal radius plating system to the distal portion of the radius bone.

12. The method of claim 11, wherein the lateral extension portion of the distal radius plating system laterally extends from the radial edge of the volar plate body at an intermediate portion of the radial edge between the proximal edge and the distal edge.

13. The method of claim 12, wherein the intermediate portion is approximately at a middle portion of the radial edge between the proximal edge and the distal edge.

14. The method of claim 11, further comprising:
introducing the distal edge of the volar head portion of the distal radius plating system to the radius bone adjacent to the lunate facet.

15. The method of claim 11, further comprising:
introducing the distal edge of the volar head portion to the radius bone in contact with a volar ulnar portion or a volar ulnar fragment of the radius bone.

16. The method of claim 11, further comprising:
introducing the distal edge of the volar head portion to the radius bone adjacent to a watershed line of the radius bone at a volar ulnar corner but not at the watershed line of the radius bone at a radial side of the radius bone.

17. The method of claim 11, wherein introducing a distal radius plating system to a distal portion of a radius bone of a patient through a volar incision on the patient includes:
introducing the volar side of the distal portion of the radius bone to a longitudinal channel on the bone-facing surface of the volar plate body.

18. The method of claim 11, wherein securing at least a portion of the distal radius plating system to the distal portion of the radius bone includes:
introducing a fixation fastener to at least one of an aperture of the plurality of apertures of the volar plate body, an aperture of the first set of apertures of the volar head portion, or the first aperture of the radial extension portion.

\* \* \* \* \*